US005401888A

United States Patent [19]

Larock

[11] Patent Number: 5,401,888
[45] Date of Patent: Mar. 28, 1995

[54] METHOD FOR PREPARING ALLYLIC ALCOHOLS

[75] Inventor: Richard C. Larock, Ames, Iowa

[73] Assignee: Iowa State University Research Foundation, Inc., Iowa

[21] Appl. No.: 15,551

[22] Filed: Feb. 9, 1993

[51] Int. Cl.$^6$ .................. C07C 29/32; C07C 33/03
[52] U.S. Cl. ..................... 568/907; 568/670; 568/866; 568/867; 568/909.5
[58] Field of Search ............ 568/866, 867, 908, 909.5, 568/670, 907, 908

[56] References Cited

U.S. PATENT DOCUMENTS

| 4,335,054 | 6/1982 | Blaser et al. | 260/465 |
| 5,004,843 | 4/1991 | Tamura et al. | 568/908 |

OTHER PUBLICATIONS

D. R. Deardorff et al., *Tetrahedron Lett.*, 26: 5615 (1985).
A. M. Echavarren et al., *J. Amer. Chem. Soc.*, 110: 4039 (1988).
R. C. Larock et al., *Comprehensive Organic Transformations*, VCH Publishers, New York (1989).
R. C. Larock et al., *J. Org. Chem.*, 55: 6244 (1990).
R. C. Larock et al., *Synlett*, No. 6: 341 (Jun. 1990).
R. C. Larock et la., *Tetrahedron Lett.*, 27: 2211 (1986).
R. C. Larock et al., *Tetrahedron Lett.*, 29: 5069 (1988).
R. C. Larock et al., *Tetrahedron Lett.*, 30: 6629 (1989).
J. A. Marshall, *Chem. Rev.*, 89: 1503 (1989).
M. Miyaura et al., *J. Organomet. Chem.*, 233 C13 (1982).
M. Oshima et al., *J. Amer. Chem. Soc.*, 111: 6280 (1989).
M. Suzuki et al., *J. Amer. Chem. Soc.*, 191: 1623 (1979).
V. M. Trost et al., *J. Amer. Chem. Soc.*, 103: 5969 (1981).
D. R. Tueting et al., *Tetrahedron Lett.*, 45: 979 (1989).

*Primary Examiner*—Werren B. Lone
*Attorney, Agent, or Firm*—Schwegman, Lundberg & Woessner

[57] ABSTRACT

The present invention provides a method for preparing allylic alcohols by the palladium-catalyzed cross-coupling of vinylic epoxides and aryl halides, vinylic halides or vinylic triflates.

20 Claims, No Drawings

METHOD FOR PREPARING ALLYLIC ALCOHOLS

BACKGROUND OF THE INVENTION

This invention was made with the support of NIH Grant No. GM40036. The U.S. Government has certain rights in this invention.

Synthetic methodology which allows for a rapid increase in molecular complexity is extremely valuable in organic chemistry, particularly when it accommodates considerable functionality. Presently, carbon-carbon bond formation catalyzed by transition metal complexes is used extensively in organic synthesis. For example, the cross-coupling of 3,4-epoxy-1-alkenes and stoichiometric amounts of organolithium, -boron, -copper, -mercury, -nickel, and -palladium compounds provides an important route to allylic alcohols (eq 1).

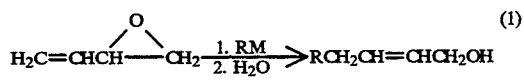

For example, see R. C. Larock, *Comprehensive Organic Transformations;* VCH Publishers, Inc., New York (1989) at pages 123–124, and J. A. Marshall et al., *Chem. Rev.*, 89, 1503 (1989). R. C. Larock et al., in *Tetrahedron Lett.*, 27, 2211 (1986) have reported one example of the analogous arylation of 4,5-epoxy-1-pentene employing stoichiometric amounts of an arylmercurial and either stoichiometric or catalytic amounts of palladium salts (eq 2).

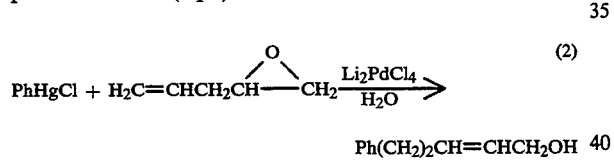

More recently, R. C. Larock et al., in *J. Org. Chem.*, 55, 6244 (1990) reported that palladium catalyzes the cross-coupling of aryl halides, but not vinylic halides, and olefinic epoxides in which the two functional groups are separated by anywhere from one to ten carbons (eq 3).

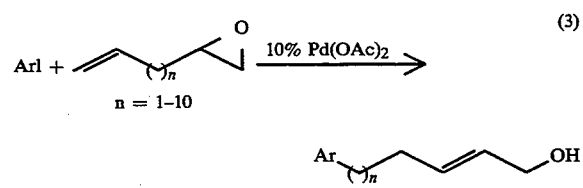

However, any attempt to extend this procedure to vinylic epoxides must circumvent the known propensity of such epoxides to react with palladium(O) to form π-allylpalladium species which can undergo attack by various nucleophiles, including formate, or rearrange to dienols or unsaturated carbonyl compounds (eq 4).

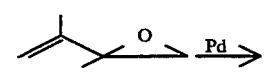

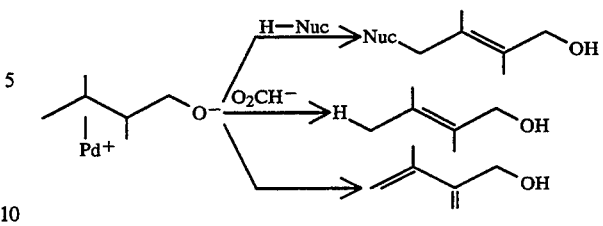

If competitive, these pathways would circumvent the desired allylic alcohol formation. For examples of such side reactions, see B. M. Trost et al., *J. Amer. Chem. Soc.*, 103, 5969 (1981); M. Oshima et al., *J. Amer. Chem. Soc.*, 111, 6280 (1989); and M. Suzuki et al., *J. Amer. Chem. Soc.*, 101, 1623 (1979). Therefore, a need exists for a method to prepare substituted allylic alcohols from vinylic epoxides and aryl or vinyl halides.

SUMMARY OF THE INVENTION

The present invention provided a synthetic method for the synthesis of allylic alcohols by the palladium-catalyzed coupling of vinylic epoxides with aryl iodides bromides, or vinylic iodides, bromides, or triflates, comprising reacting a compound of the formula (a) ArY, wherein Ar is a substituted aryl or unsubstituted aryl moiety and Y is I or Br or (b) $(R^1)(R^2)C=C(R^3)X$, wherein X is Br, I or trifluoromethanesulfonyloxy, and $R^1$, $R^2$ and $R^3$ are individually H, $(C_1-C_8)$alkyl, preferably $(C_1-C_4)$alkyl; Ar, Ar$(C_1-C_4)$alkyl or $R^1$ and $R^3$ taken together are $-(CH_2)_q-$, wherein q is at least 3, preferably 3-6; with a vinylic epoxide of the formula (I):

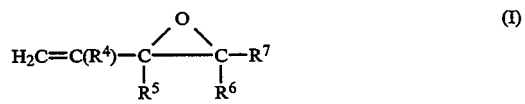

wherein $R^4$, $R^5$, $R^6$ and $R^7$ are individually H, Ar or $(C_1-C_8)$-alkyl, preferably $(C_1-C_4)$ alkyl; preferably $R^4$, $R^5$, $R^6$ and $R^7$ are H, phenyl or $(C_1-C_2)$alkyl; in the presence of effective amounts of a Pd catalyst, preferably a Pd(II) catalyst, an organic base, a formate and a chloride ion source, in an organic solvent, to yield an allylic alcohol of the general formula (II):

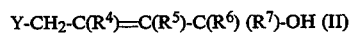

wherein Y is Ar or is the moiety $(R^1)(R^2)C=C(R^3)-$, wherein Ar, $R^1$, $R^2$, $R^3$, $R^4$, $R^5$, $R^6$ and $R^7$ are as defined above. Preferably, one of $R^1$ $R^2$ and $R^3$ is $(C_1-C_4)$alkyl and two are H; or $R^1$ and $R^3$ taken together are $-(CH_2)_3-$ or $-(CH_2)_4-$ and $R^2$ is H. Preferably, two of $R^4$, $R^5$, $R^6$ and $R^7$ are H, most preferably two of $R^4$, $R^5$, $R^6$ and $R^7$ are also $(C_1-C_4)$alkyl or phenyl.

In fact, the upper limits on the molecular weights of ArY, $(R^1)(R^2)C=C(R^3)X$, compound I and compound II are controlled only by physical or practical considerations, such as the solubility of the starting materials, the cost of the starting materials, the reaction conditions and the like.

The formation of the compounds of formula II is apparently initiated by formation of ArPdI, ArPdBr or $(R^1)(R^2)C=C(R^3)PdX$, insertion of this species into the olefinic bond of compound (I), ring opening of the epoxide to yield a palladium alkoxide and reduction to alcohol (II) by the formate salt, simultaneously regenerating the Pd catalyst. In view of the potential side reactions depicted in equation 4, the high yields of E/Z mixtures of single products of greater than 50%, preferably greater than 70% and most preferably greater than 80%, were unexpected. Also, unlike the earlier process for the arylation of olefinic epoxides, reported by Larock et al., in *J. Org. Chem.*, 55, 6244 (1990), which failed with vinylic halides, under the present procedure vinylic iodides, bromides, and triflates react with vinylic epoxides to produce dienols in good yield. With vinylic iodides, best results are obtained using the less hindered vinylic iodides.

The compounds of formula II can be utilized directly, e.g., as substituted unsaturated monomers for the preparation of aralkyl-substituted polymers, or can be utilized indirectly as intermediates in the synthesis of more complex bioactive compounds. Cleavage of the double bond or bonds in compounds of formula II can yield arylalkanoic acids, or dialkanoic acids.

DETAILED DESCRIPTION OF THE INVENTION

A wide variety of substituted and unsubstituted aryl iodides (ArI) or aryl bromides (ArBr) can be employed in the present process, and the Ar("aryl") substituent(s) on the vinylic iodide, vinylic bromide, or vinylic triflate and/or on the vinylic epoxide (I) can likewise be substituted or unsubstituted. Preferably, Ar is a $C_6$–$C_{10}$ aryl moiety, such as phenyl, naphthyl, 2- or 3-thienyl, 2- or 3-furyl, 2-, 3- or 4-pyridyl and the like. A wide variety of 1–3 non-iodo substituents can be present on the aryl ring, including Ar, Br, Cl, F, formyl, amino, nitro, —CH(OCH$_3$)$_2$, —CH(OEt)$_2$, —CO$_2$R, —CN, ($C_1$–$C_4$)alkyl, ($C_1$–$C_4$)alkoxy, ArO-, 3,4-methylene-dioxy, ($C_1$–$C_4$)alkoxycarbonyl, ($C_1$–$C_4$)alkylcarbonyl, hydroxy($C_1$–$C_4$)alkyl, (R)(R)N and (R)S-, wherein each R is ($C_1$–$C_4$)alkyl, phenyl or mixtures thereof. Other representative Ar-substituents are given in Blaser et al. (U.S. Pat. No. 4,335,054), the disclosure of which is incorporated by reference herein, at Col. 2, line 19 to Col. 3, line 3. The substituents on Ar are preferably electron-donating, such as hydroxy($C_1$–$C_4$)-alkyl, ($C_1$–$C_4$)alkoxy or ($C_1$–$C_4$)alkyl, and the like. As used throughout, the term "alkyl" includes branched or straight-chain alkyl. Preferably, Ar is phenyl or is substituted with ($C_1$–$C_4$)alkoxy, 3,4-methylene-dioxy, 3,4,5-(tris)methoxy, hydroxymethyl and the like.

The palladium(II) (Pd(II)) catalyst is generally employed in an amount of about 0.001–20 mol-%, preferably about 5–15 mol-%, based on the aryl bromide or aryl iodide, vinylic iodide, bromide, or vinylic triflate. Useful catalysts include PdCl$_2$, Pd(OAc)$_2$, PdBr$_2$, Pd(CN)$_2$, Pd(NO$_3$)$_2$ and the like. Other Pd catalysts which can be used in the present method include those disclosed in Blaser et al. (U.S. Pat. No. 4,335,054) at Col. 6, line 5 to Col. 7, line 3, as well as Pd(O) catalysts such as Pd(dba)$_2$ and Pd(PPh$_3$)$_4$.

Organic bases preferred for use in the present process are those which are adequately soluble in the reaction medium. Representative bases are disclosed at Col. 7, lines 8–65 of the Blaser et al. patent. The preferred organic bases are trialkylamines or dicycloalkyl(alkyl)amines of about 6–20 carbon atoms. These include triethylamine, diethyl(methyl)amiine, dimethyl(isopropyl)amine, diisopropyl(ethyl)amine, dicyclohexyl(ethyl)amine and the like.

A source of halide, preferably of chloride (Cl$^-$), is also preferably employed in the present process, and can act to increase both the reaction rates and the yields. Preferred chloride sources are tetra($C_1$–$C_{22}$)alkyl- or tetraaryl ammonium chlorides, tetra($C_1$–$C_{20}$)alkyl or tetraaryl phosphonium chlorides and alkali metal chlorides, including tetra-n-butylammonium chloride (n-Bu$_4$NCl) and lithium chloride.

A formate salt is employed as an in situ reducing agent. Preferred formates include those of the formula $M^+ {}^-O_2CH$, wherein $M^+$ is Li$^+$, Na$^+$, K$^+$ or ammonium, i.e., (R$_4$N)$^+$ or (R$_3$NH)$^+$, wherein R is as defined above.

Preferably, the aromatic iodide or bromide, or the vinylic iodide, bromide, or vinylic triflate are combined with a molar excess of the vinylic epoxide of formula (I) (mole ratio of about 1:2.5–7.5) with the Pd(II) or Pd(O) catalyst and excess molar amounts of the formate (1:2.5–7.5 equiv), chloride ion (1.5–2.5 equiv) and organic amine (1.5–5 equiv) in a suitable organic solvent. Preferred organic solvents are those which are polar. These include ($C_1$–$C_4$)alkanols, tetrahydrofuran (THF), methylene chloride, acetonitrile, ethers, glycol ethers, dimethylformamide, dimethylacetamide, hexamethylphosphoramide, dimethylsulfoxide and mixtures thereof.

The reaction mixture is stirred for about 5–50 hrs at about 60° C.–120° C., or until the reaction has gone to completion, or otherwise reached equilibrium. The product is then isolated, by partition of the reaction mixture between ether and aqueous NH$_4$Cl, so as to extract the product into the ether, followed by distillation, chromatography and the like.

The invention will be further described by reference to the examples as summarized on Table I, below. These examples were carried out using the following experimental procedure.

EXAMPLE 1

Preparation of (E)- and (Z)-2-Methyl-4-phenyl-2-buten-1-ol.

To an oven-dried 25 ml round-bottom flask containing a magnetic stirrer were added the following reagents: palladium acetate (11.3 mg, 0.05 mmol), sodium formate (170 mg, 2.5 mmol), tetra-n-butylammonium chloride (277 mg, 1.0 mmol), diisopropylethylamine (0.26 ml, 1.5 mmol), iodobenzene (102 mg, 0.5 mmol), 3,4-epoxy-3-methyl-1-butene (210 mg, 2.5 mmol), and N,N-dimethylacetamide (2.0 ml). The solution was stirred at 80° C. for 1 day. Ether (15 ml) was then added to the reaction mixture. The ether layer was washed with saturated aqueous ammonium chloride (15 ml×2), and the combined aqueous layers were back extracted with ether (15 ml×2). The combined ether fractions were dried over anhydrous magnesium sulfate. After removal of the solvents, the residue was purified by flash column chromatography on silica gel using a 10:1 mixture of hexane to ethyl acetate as eluents. (E)- and (Z)-2-Methyl-4-phenyl-2-buten-1-ol were obtained in 71% yield as a colorless liquid.

Employing the procedure of Example 1, and the reagents listed in Table I, the allylic alcohols listed in Table I were prepared.

TABLE I

Palladium-Catalyzed Cross-Coupling of Vinylic Epoxides and Organic Halides or Triflates

| entry | epoxide | organic halide or triflate | product | % isolated yield | E/Z ratio[a] |
|---|---|---|---|---|---|
| 1 | (vinyl epoxide) | 2-iodobenzyl alcohol | 2-(4-hydroxy-2-butenyl)benzyl alcohol | 70 | 69:31 |
| 2 | | 2-iodoanisole | 2-(4-hydroxy-2-butenyl)anisole | 75 | 60:40 |
| 3 | | 2-iodonaphthalene | 2-(4-hydroxy-2-butenyl)naphthalene | 65 | 59:41 |
| 4 | | ethyl 4-iodobenzoate | ethyl 4-(4-hydroxy-2-butenyl)benzoate | 41 | 63:37[b] |
| 5 | (methyl vinyl epoxide) | 3,4,5-trimethoxyiodobenzene | product | 72 | 52:48 |
| 6 | (vinyl epoxide) | 3,4,5-trimethoxyiodobenzene | product | 51 | 73:27 |
| 7 | (isoprene epoxide) | iodobenzene | 4-phenyl-3-methyl-2-buten-1-ol | 24 | 41:59 |
| 8 | (vinyl epoxide) | (CH₃)₃C-CH=CH-I (E) | (CH₃)₃C-CH=CH-CH₂-CH=CH-CH₂OH | 85 | 50:50 |
| 9 | | 2-iodo-1-hexene (n-C₄H₉) | n-C₄H₉ dienol | 37 | 64:46 |
| 10 | | 1-iodocyclohexene | 1-cyclohexenyl dienol | 62 | 55:45[c] |
| 11 | (vinyl epoxide) | n-C₄H₉-CH=CH-I (Z) | n-C₄H₉ dienol | 91 | 72:27 |
| 12 | | Ph-CH=CH-I (Z) | Ph dienol | 77 | 77:23 |

TABLE I-continued

Palladium-Catalyzed Cross-Coupling of Vinylic Epoxides and Organic Halides or Triflates

| entry | epoxide | organic halide or triflate | product | % isolated yield | E/Z ratio[a] |
|---|---|---|---|---|---|
| 13 | | n-C4H9, I / C=C / H, H | n-C4H9—=—/=\—OH | 61 | 72:28 |
| 14 | /\/\O/\/ | n-C4H9, H / C=C / H, I | n-C4H9—/=\—/=\—OH (with branch) | 71 | 50:50 |
| 15 | /\/\O/\/ | (cyclohexenyl)-OTf | (cyclohexylidene)-CH2-CH=CH-OH | 45 | 78:22 |

[a]Determined by integration of the 300 MHz $^1$H NMR spectral peaks corresponding to the allylic hydrogens next to the hydroxyl group.
[b]Only 1 equiv NaO$_2$CH was used.
[c]Reaction time is 2 days.

As can be seen from the data in Table I, a wide variety of aryl iodides may be employed in this process. The best yields are obtained using electron-rich arenes. Aryl halides bearing electron-withdrawing substituents give lower yields, but can still be used successfully.

The yields of alcohols also vary significantly with the structure of the vinylic epoxide. When aryl halides are employed, 3,4-epoxy-3-methyl-1-butene (entries 1–4) and 3,4-epoxy-3-methyl-1-pentene (entry 5) were found to give significantly higher yields than 3,4-epoxy-1-butene (entry 6), while 3,4-epoxy-2-methyl-1-butene (entry 7) with a more substituted carbon-carbon double bond gave a lower yield. In the latter case, it is assumed that the increased steric hindrance to alkene insertion now favors one or more of the side reactions suggested previously. However, with vinylic halides, the yields obtained from 3,4-epoxy-1-butene (entries 11–13) are usually higher than those obtained from 3,4-epoxy-3-methyl-1-butene (entries 8–10) or 3,4-epoxy-3-methyl-1-pentene (entry 14).

The stereochemistry of the vinylic halide is retained during cross-coupling. However, when using aryl or vinylic halides, there is only modest control of the stereochemistry in the newly generated carbon-carbon double bond. The stereoselectivity depends on the structure of the vinylic epoxide employed. Disubstituted double bonds are usually generated in approximately a 3:1 E/Z ratio. Trisubstituted double bonds are produced with stereo-selectivities ranging from zero to approximately 2:1. The stereoisomer favored, however, depends on the substitution pattern of the epoxide.

All publications cited herein are hereby incorporated by reference. The invention has been described with reference to various specific and preferred embodiments and techniques. However, it should be understood that many variations and modifications may be made while remaining within the spirit and scope of the invention.

What is claimed is:

1. A method for preparing allylic alcohols comprising reacting (a) ArI or ArBr, wherein Ar is substituted aryl or unsubstituted aryl or (b) a compound of the formula $(R^1)(R^2)C=C(R^3)X$, wherein X is I or Br, or trifluoromethanesulfonyloxy, and $R^1$ $R^2$ and $R^3$ are H, (C$_1$-C$_8$) alkyl, Ar, Ar (C$_1$-C$_4$) alkyl or $R^1$ and $R^3$ taken together are —(CH$_2$)$_q$—, wherein q is at least 3; with a vinylic epoxide of the formula (I):

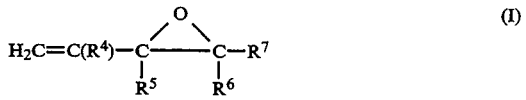

wherein $R^4$, $R^5$, $R^6$ and $R^7$ are individually H, Ar or (C$_1$-C$_8$)alkyl, in the presence of effective amounts of a Pd catalyst, an organic base, a formate and a chloride ion source, in an organic solvent, to yield an allylic alcohol of the general formula (II):

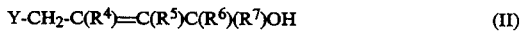

wherein Y is Ar or $(R^1)(R^2)C=C(R^3)$-, wherein Ar, $R^1$, $R^2$, $R^3$, $R^4$, $R^5$, $R^6$ and $R^7$ are as defined above 2. The method of claim 1 wherein two of $R^4$, $R^5$, $R^6$ and $R^7$ are H.

3. The method of claim 2 wherein two of $R^4$, $R^5$, $R^6$ and $R^7$ are (C$_1$-C$_4$)alkyl or phenyl.

4. The method of claim 1 wherein Ar is phenyl or phenyl substituted with 1–3 substituents selected from the group consisting of (C$_1$-C$_4$)alkyl, hydroxy(C$_1$-C$_4$)alkyl and (C$_1$-C$_4$)alkoxy.

5. The method of claim 4 wherein Ar is phenyl.

6. The method of claim 1 wherein the catalyst is a Pd(II) catalyst.

7. The method of claim 6 wherein the Pd(II) catalyst is Pd(OAc)$_2$.

8. The method of claim 1 wherein the organic base is a trialkylamine or a dicycloalkyl(alkyl)amine of about 6–20 carbon atoms.

9. The method of claim 1 wherein the reaction is carried out at about 60°–120° C. for about 5–50 hours.

10. The method of claim 1 wherein the reaction is carried out in dimethylacetamide.

11. The method of claim 1 wherein the chloride ion source is a tetraalkylammonium chloride.

12. The method of claim 11 wherein the tetraalkylammonium chloride is (n-Bu)$_4$NCl.

13. The method of claim 1 wherein the formate is an alkali metal salt of formic acid.

14. The method of claim 1 where X is I.

15. The method of claim 1 wherein Ar is substituted with substituents chosen from a group consisting of Ar, Br, $C_1$, F, formyl, amirto, nitro, —$CH(OCH_3)_2$, —$CH(OEt)_2$, —$CO_2R$, ($C_1$–$C_4$)alkylcarbonyl, ($C_1$–$C_4$)alkoxycarbonyl, hydroxy($C_1$–$C_4$)alkyl, 3,4-methylene-dioxy, —$CO_2$phenyl, —CN, ($C_1$–$C_{10}$)alkyl, ($C_1$–$C_{14}$)alkoxy, ArO—, di-($C_{1-10}$-alkyl)amino, chloromethyl, trifluoromethyl, ($C_1$–$C_4$)alkylsulfonyl, —$COC_{1-10}$-alkyl and —CO-phenyl wherein R is chosen from a group consisting of ($C_1$–$C_4$)alkyl, phenyl or mixtures thereof.

16. The method of claim 1 wherein the Pd(II) catalyst is chosen from the group consisting of $PdCl_2$, $Pd(OAc)_2$, $PdBr_2$, $Pd(CN)_2$, $Pd(NO_3)_2$, $Pd(OOCCH_3)_2$, $Pd(O_2CC_{1-12}$-alkyl$)_2$, $Pd(CH_3COCHCOCH_3)_2$, $[Pd(NH_3)]_4Cl_2$, $[PdCl_4]Na_2$, $Pd(OOCCH3)2(2,2'$-bipyridyl), $Pd(OOCCH_3)_2$(o-phenanthroline), $PdCl_2[OS(CH_3)_2]_2$, and $PdCl_2(NC\text{-}phenyl)_2$.

17. The method of claim 1 wherein the Pd(0) catalyst is chosen from a group consisting of $Pd(dba)_2$ and $Pd(PPh_3)_4$.

18. The method of claim 1 wherein the organic base is a trialkylamine or dicycloalkyl(alkyl)amine of about 6–20 carbon atoms.

19. A method for preparing allylic alcohols comprising reacting (a) ArI or ArBr, or (b) a compound of the formula $(R^1)(R^2)C=C(R^3)X$, wherein X is I, Br, or trifluoromethanesulfonyloxy, and $R^1$, $R^2$ and $R^3$ are H, ($C_1$–$C_8$)alkyl, Ar, Ar($C_1$–$C_4$) alkyl or $R^1$ and $R^3$ taken together are —$(CH_2)_q$—, wherein q is at least 3; with a vinylic epoxide of the formula (I):

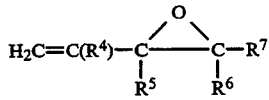  (I)

wherein $R^4$, $R^5$, $R^6$ and $R^7$ are individually H, Ar or ($C_1$–$C_8$) alkyl, in the presence of effective amounts of a Pd(0) or Pd(II) catalyst, an organic base that is soluble in the reaction media, a formate of the formula $M+O_2CH—$, wherein M is an alkali metal or ammonium salt, and a chloride ion source chosen from a group consisting of tetra($C_1$–$C_{22}$)alkyl- or tetraaryl ammonium chlorides, tetra($C_1$–$C_{20}$)alkyl or tetraaryl phosphonium chlorides and alkali metal chlorides, in an organic solvent, to yield an allylic alcohol of the general formula (II):

$$Y\text{-}CH_2\text{-}C(R^4)=C(R^5)C(R^6)(R^7)OH \qquad (II)$$

wherein Y is Ar or $(R^1(R^2)C=C(R^3)$-, wherein $R^1$, $R^2$, $R^3$, $R^4$, $R^5$, $R^6$, and $R^7$ are as defined above and Ar is a substituted or unsubstituted ($C_6$–$C_{10}$) aryl.

20. A method for preparing allylic alcohols comprising reacting (a) ArI or ArBr, or (b) a compound of the formula $(R^1)(R^2)C=C(R^3)X$, wherein X is 1, Br, or trifluoromethanesulfonyloxy, and $R^1$, $R^2$ and $R^3$ are H, ($C_1$–$C_8$)alkyl, Ar, Ar($C_1$–$C_4$)alkyl or $R^1$ and $R^3$ taken together are —$(CH_2)_q$—, wherein q is at least 3; with a vinylic epoxide of the formula (I):

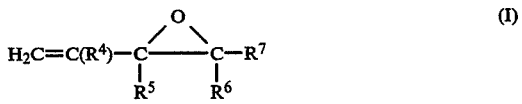  (I)

wherein $R^4$, $R^5$, $R^6$ and $R^7$ are individually H, Ar or ($C_1$–$C_8$)alkyl, in the presence of effective amounts of a Pd(0) or Pd(II) catalyst, an organic base chosen from a group consisting of a trialkyl amine or a dicycloalkyl(alkyl)amine of about 6–20 carbon atoms, a formate of the formula $M+O_2CH—$, wherein M is chosen from a group consisting of Li+, Na+, K+ or ammonium, and a chloride ion source chosen from a group consisting of a tetra($C_1$–$C_{22}$)alkyl- or a tetraaryl ammonium chloride, tetra($C_1$–$C_{20}$)alkyl or tetraaryl phosphonium chloride and alkali metal chloride, in an organic solvent, to yield an allylic alcohol of the general formula (II):

$$Y\text{-}CH_2\text{-}C(R^4)=C(R^5)C(R^6)(R^7)OH \qquad (II)$$

wherein Y is Ar or $(R^1(R^2)C=C(R^3)$-, wherein $R^1$, $R^2$, $R^3$, $R^4$, $R^5$, $R^6$, and $R^7$ are as defined above and wherein Ar is a substituted or unsubstituted ($C_6$–$C_{10}$)aryl and the substituents are chosen from the group consisting of Ar, Br, $C_1$, F, formyl, amino, nitro, —$CH(OCH_3)_2$, —$CH(OEt)_2$, —$CO_2R$, —CN, ($C_1$–$C_4$)alkyl, ($C_1$–$C_4$)alkoxy, ArO-, 3,4-methylene-dioxy, ($C_1$–$C_4$)alkoxycarbonyl, hydroxy($C_1$–$C_4$)alkyl, (R)(R)N and (R)S-, wherein each R is ($C_1$–$C_4$) alkyl or phenyl.

* * * * *

UNITED STATES PATENT AND TRADEMARK OFFICE
CERTIFICATE OF CORRECTION

PATENT NO. : 5,401,888
DATED : March 28, 1995
INVENTOR(S) : Larock

It is certified that error appears in the above-indentified patent and that said Letters Patent is hereby corrected as shown below:

Column 2, line 7, insert -- ⌒ --. (in formula).

Column 9, line 3, delete "$_1$", and insert --1--.

Column 9, line 3, delete "amirto" and insert --amino--.

Column 10, line 41, delete "$_1$", and insert "1".

Signed and Sealed this

Seventeenth Day of October, 1995

Attest:

BRUCE LEHMAN

*Attesting Officer*       *Commissioner of Patents and Trademarks*